US011452694B2

(12) United States Patent
Licht et al.

(10) Patent No.: US 11,452,694 B2
(45) Date of Patent: Sep. 27, 2022

(54) HIGH CONCENTRATION DOSAGE FORMS OF PRIDOPIDINE (71) Applicant: PRILENIA NEUROTHERAPEUTICS LTD., Herzliya (IL)

(72) Inventors: Danit Licht, Givat Shmuel (IL); Ioana Lovinger, Kfar Saba (IL)

(73) Assignee: Prilenia Neurotherapeutics Ltd., Herzliya (IL)

( * ) Notice: Subject to any disclaimer, the term of this patent is extended or adjusted under 35 U.S.C. 154(b) by 58 days.

(21) Appl. No.: 16/803,145

(22) Filed: Feb. 27, 2020

(65) Prior Publication Data

US 2020/0188305 A1 Jun. 18, 2020

Related U.S. Application Data (63) Continuation-in-part of application No. PCT/US2018/048831, filed on Aug. 30, 2018.

(60) Provisional application No. 62/552,071, filed on Aug. 30, 2017.

(51) Int. Cl.
*A61K 31/451* (2006.01)
*A61K 9/20* (2006.01)
*A61K 9/48* (2006.01)

(52) U.S. Cl.
CPC .......... *A61K 9/2054* (2013.01); *A61K 9/2013* (2013.01); *A61K 9/2072* (2013.01); *A61K 9/4825* (2013.01); *A61K 9/4858* (2013.01); *A61K 9/4866* (2013.01); *A61K 31/451* (2013.01)

(58) Field of Classification Search
None
See application file for complete search history.

(56) References Cited

U.S. PATENT DOCUMENTS

| | | | |
|---|---|---|---|
| 6,903,120 | B2 | 6/2005 | Sonesson et al. |
| 7,923,459 | B2 | 4/2011 | Gauthier et al. |
| RE46,117 | E | 8/2016 | Sonesson et al. |
| 2003/0139423 | A1 | 7/2003 | Sonesson et al. |
| 2006/0135531 | A1 | 6/2006 | Sonesson et al. |
| 2010/0105736 | A1 | 4/2010 | Wikström |
| 2013/0150406 | A1 | 6/2013 | Zimmermann et al. |
| 2013/0197031 | A1 | 8/2013 | Sonesson |
| 2013/0267552 | A1 | 10/2013 | Waters et al. |
| 2014/0315951 | A1 | 10/2014 | Sonesson et al. |
| 2014/0378508 | A1 | 12/2014 | Bassan et al. |
| 2015/0202302 | A1 | 7/2015 | Licht et al. |
| 2015/0209344 | A1 | 7/2015 | Zimmermann et al. |
| 2015/0374677 | A1 | 12/2015 | Schmidt et al. |
| 2016/0095847 | A1 | 4/2016 | Sonesson |
| 2016/0166559 | A1 | 6/2016 | Sonesson |
| 2016/0176821 | A1 | 6/2016 | Wu et al. |
| 2016/0243098 | A1 | 8/2016 | Geva et al. |
| 2017/0020854 | A1 | 1/2017 | Licht et al. |
| 2017/0022158 | A1 | 1/2017 | Barel et al. |

FOREIGN PATENT DOCUMENTS

| | | | |
|---|---|---|---|
| WO | WO 2001/046145 A1 | 6/2001 |
| WO | WO 2006/040155 A1 | 4/2006 |
| WO | WO 2008/127188 A1 | 10/2008 |
| WO | WO 2012/002863 A1 | 1/2012 |
| WO | WO 2013/034622 A1 | 3/2013 |
| WO | WO 2013/086425 A1 | 6/2013 |
| WO | WO 2013/152105 A1 | 10/2013 |
| WO | WO 2014/205229 A1 | 12/2014 |
| WO | WO 2015/112601 A1 | 7/2015 |
| WO | WO 2016/003919 A1 | 1/2016 |
| WO | WO 2016/138130 A1 | 9/2016 |
| WO | WO 2016/138135 A1 | 9/2016 |
| WO | WO 2017/015609 A1 | 1/2017 |
| WO | WO 2017/015615 A1 | 1/2017 |

OTHER PUBLICATIONS https://www.1fatabletpresses.com/articles/overview-of-disintegrants retrieved on Feb. 10, 2022.*
ClinicalTrials.gov Identifier: NCT02006472 "A Phase 2, to Evaluating the Safety and Efficacy of Pridopidine Versus Placebo for Symptomatic Treatment in Patients With Huntington's Disease" 2013 (updated 2019).
CSID:25948790, http://www.chemspider.com/Chemical-Structure.25948790.html (accessed 23:27, Jul. 15, 2016).
CSID:7971505, http://www.chemspider.com/Chemical-Structure.7971505.html (accessed 23:33, Jul. 15, 2016).
De Yebenes et al. "Pridopidine for the treatment of motor function in patients with Huntington's disease (MermaiHD): a phase 3, randomised, double-blind, placebo-controlled trial" The Lancet Neurology. Dec. 1, 2011;10(12):1049-57.
Geva et al. "Pridopidine activates neuroprotective pathways impaired in Huntington Disease" Human molecular genetics. Sep. 15, 2016;25(18):3975-87.
Huntington Study Group Hart Investigators. "A randomized, double-blind, placebo-controlled trial of pridopidine in Huntington's disease" Movement Disorders. Sep. 2013;28(10):1407-15.
Krog et al. "Pharmacokinetic and tolerability profile of pridopidine in healthy-volunteer poor and extensive CYP2D6 metabolizers, following single and multiple dosing" European journal of drug metabolism and pharmacokinetics. Mar. 1, 2013;38(1):43-51.
Mangal et al. "Superdisintegrants: an updated review" International journal of pharmacy and pharmaceutical science research. 2012;2(2):26-35.

(Continued)

Primary Examiner — Jessica Worsham
(74) Attorney, Agent, or Firm — Mark S. Cohen; Pearl Cohen Zedek Latzer Baratz LLP (57) ABSTRACT The subject invention provides a solid unit dosage form comprising pridopidine or pharmaceutically acceptable salt thereof and at least one pharmaceutically acceptable excipient, wherein the dosage form has a volume and wherein the ratio of the amount of pridopidine to the volume of the dosage form is 135-600 mg/ml.

26 Claims, 2 Drawing Sheets (56) References Cited

OTHER PUBLICATIONS

McGarry et al. "Safety and exploratory efficacy at 36 months in Open-HART, an open-label extension study of pridopidine in Huntington's disease" Journal of Huntington's disease. Jan. 1, 2017;6(3):189-99.
Mohanachandran et al. "Superdisintegrants: an overview" International journal of pharmaceutical sciences review and research. Feb. 2011;6(1):105-9.
Osterberg et al. "A single-center, randomized, placebo-controlled, double-blind study to evaluate the safety, tolerability, and pharmacokinetics of multiple-ascending doses of pridopidine in healthy volunteers" In Neurotherapeutics Jan. 1, 2013 (vol. 10, No. 1, pp. 175-175).
Rabinovich-Guilatt et al., "The effect of mild and moderate renal impairment on the pharmacokinetics of pridopidine, a new drug for Huntington's disease" British journal of clinical pharmacology. Feb. 2016;81(2):246-55.
Ryskamp et al. "The sigma-1 receptor mediates the beneficial effects of pridopidine in a mouse model of Huntington disease" Neurobiology of disease. Jan. 1, 2017;97:46-59.
USP <711> 33(4) Fourth Interim Revision Announcement: Dissolution http://www.usppf.com/pf/pub/index.html 1/15 711 Dissolution, 2016.

* cited by examiner

HIGH CONCENTRATION DOSAGE FORMS OF PRIDOPIDINE

CROSS REFERENCE TO RELATED APPLICATIONS

This application is a continuation-in-part Application from International Patent Application PCT/US2018/048831 filed Aug. 30, 2018, which claims the benefit of U.S. Provisional Application No. 62/552,071, filed Aug. 30, 2017 the entire contents of each which are hereby incorporated by reference.

BACKGROUND OF THE INVENTION

Pridopidine (Huntexil®) is a drug in development for the treatment of patients with Huntington's disease. The chemical name of pridopidine base is 4-(3-(Methylsulfonyl)phenyl)-1-propylpiperidine, and its Chemical Registry Number is CAS 346688-38-8 (CSID:7971505 2016). The Chemical Registry number of pridopidine hydrochloride is 882737-42-0 (CSID:25948790 2016). Processes of synthesis of pridopidine and a pharmaceutically acceptable salt thereof are disclosed in U.S. Pat. No. 7,923,459. U.S. Pat. No. RE46117 claims pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

US Patent Application Publication Nos. 20140378508 and 20150202302, describe methods of treatment with high doses of pridopidine and modified release formulations of pridopidine, respectively.

Pridopidine was shown to enhance secretion of the neuroprotective brain-derived neurotrophic factor (BDNF) in a neuroblastoma cell line, in a SIR-dependent manner (Geva 2016).

There remains an unmet need for high dose immediate release formulations of pridopidine.

BRIEF SUMMARY OF THE INVENTION

Provided herein is a solid unit dosage form comprising pridopidine and at least one pharmaceutically acceptable excipient, wherein the dosage form has a volume and wherein the ratio of the amount of pridopidine to the volume of the dosage form is 135-600 mg/ml.

The present invention further provides processes for the preparation of the dosage forms, packages and kits comprising said dosage forms and methods of using said dosage forms.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The present invention is based in part on the finding that pridopidine is not easily formulated into high dose immediate release dosage forms using standard dry blend formulation methods. Additionally, the dosage form must be suitable for use by a patient population that often suffers from both dysphagia and movement disorders. Therefore, factors such as the type and the size of the dosage form, must be taken into consideration in designing a dosage form suitable for such a patient population. For example, the dosage form should be large enough to handle, yet small enough for a patient to easily swallow. The dosage forms included in this invention are immediate release formulations that are useful in treating patients requiring high doses (>45 mg day) of pridopidine.

The subject invention provides a solid unit dosage form comprising pridopidine and at least one pharmaceutically acceptable excipient, wherein the dosage form has a volume and wherein the ratio of the amount of pridopidine to the volume of the dosage form is 135-600 mg/ml. In one embodiment, the ratio of the amount of pridopidine to the volume of the dosage form is 135-500 mg/ml. In another embodiment, the ratio of the amount of pridopidine to the volume of the dosage form is 175-370 mg/ml.

In another embodiment, the solid unit dosage form comprises about 67.5 mg, about 75 mg, about 90 mg, about 100 mg, about 112.5 mg, about 125 mg, about 135 mg, about 150 mg, 175 mg, about 180 mg or about 200 mg of pridopidine base, or the equivalent in the form of pridopidine HCl or any other pridopidine salt. In a further embodiment, the volume of the dosage form is about 0.5 ml and the solid unit dosage form comprises about 90 mg-200 mg pridopidine;

the volume of the dosage form is about 0.41 ml and the solid unit dosage form comprises about 125 mg-175 mg pridopidine, or the volume of the dosage form is 0.37 ml and the solid unit dosage form comprises 67.5-200 mg pridopidine;

the volume of the dosage form is 0.30 ml and the solid unit dosage form comprises 67.5-180 mg pridopidine;

the volume of the dosage form is 0.21 ml and the solid unit dosage form comprises 67.5-135 mg pridopidine; or the volume of the dosage form is 0.13 ml and the solid unit dosage form comprises 67.5 mg pridopidine.

In some embodiments, the volume of the solid unit dosage form is 0.37 ml and the solid unit dosage form comprises 75 mg pridopidine. In some embodiments, the volume of the solid unit dosage form is 0.3 ml and the solid unit dosage form comprises 75 mg pridopidine.

In some embodiments, the volume of the solid unit dosage form is 0.37 ml and the solid unit dosage form comprises 100 mg pridopidine. In some embodiments, the volume of the solid unit dosage form is 0.3 ml and the solid unit dosage form comprises 100 mg pridopidine.

In one embodiment, the solid unit dosage form comprises 67.5 mg of pridopidine (pridopidine base or equivalent as pridopidine salt). In one embodiment, the solid unit dosage form comprises 75 mg of pridopidine. In one embodiment, the solid unit dosage form comprises 90 mg of pridopidine. In one embodiment, the solid unit dosage form comprises 100 mg of pridopidine. In another embodiment, the solid unit dosage form comprises 112.5 mg of pridopidine. In one embodiment, the solid unit dosage form comprises 125 mg of pridopidine. In one embodiment, the solid unit dosage form comprises 135 mg of pridopidine. In one embodiment, the solid unit dosage form comprises 150 mg of pridopidine. In one embodiment, the solid unit dosage form comprises 175 mg of pridopidine. In one embodiment, the solid unit dosage form comprises 180 mg of pridopidine. In one embodiment, the solid unit dosage form comprises 200 mg of pridopidine.

In some embodiments the volume of the dosage form is about 0.21 ml and the solid unit dosage form comprises about 67.5 mg to about 135 mg pridopidine. In a further embodiment, the volume of the dosage form is about 0.21 ml and the solid unit dosage form comprises 67.5 mg pridopidine. In an additional embodiment, the volume of the dosage form is about 0.21 ml and the solid unit dosage form comprises 75 mg pridopidine. In another embodiment, the volume of the dosage form is about 0.21 ml and the solid unit dosage form comprises 90 mg pridopidine. In an additional embodiment, the volume of the dosage form is about 0.21 ml and the solid unit dosage form comprises 100 mg pridopidine. In a further embodiment, the volume of the dosage form is about 0.21 ml and the solid unit dosage form comprises 112.5 mg pridopidine. In an additional embodiment, the volume of the dosage form is about 0.21 ml and the solid unit dosage form comprises 125 mg pridopidine. In another embodiment, the volume of the dosage form is about 0.21 ml and the solid unit dosage form comprises 135 mg pridopidine.

In some embodiments the volume of the dosage form is about 0.3 ml and the solid unit dosage form comprises about 67.5 mg to about 200 mg pridopidine. In a further embodiment, the volume of the dosage form is about 0.3 ml and the solid unit dosage form comprises 67.5 mg pridopidine. In an additional embodiment, the volume of the dosage form is about 0.3 ml and the solid unit dosage form comprises 75 mg pridopidine. In another embodiment, the volume of the dosage form is about 0.3 ml and the solid unit dosage form comprises 90 mg pridopidine. In an additional embodiment, the volume of the dosage form is about 0.3 ml and the solid unit dosage form comprises 100 mg pridopidine. In a further embodiment, the volume of the dosage form is about 0.3 ml and the solid unit dosage form comprises 112.5 mg pridopidine. In an additional embodiment, the volume of the dosage form is about 0.3 ml and the solid unit dosage form comprises 125 mg pridopidine. In another embodiment, the volume of the dosage form is about 0.3 ml and the solid unit dosage form comprises 135 mg pridopidine. In an additional embodiment, the volume of the dosage form is about 0.3 ml and the solid unit dosage form comprises 150 mg pridopidine. In an additional embodiment, the volume of the dosage form is about 0.3 ml and the solid unit dosage form comprises 175 mg pridopidine. In an additional embodiment, the volume of the dosage form is about 0.3 ml and the solid unit dosage form comprises 180 mg pridopidine. In an additional embodiment, the volume of the dosage form is about 0.3 ml and the solid unit dosage form comprises 200 mg pridopidine.

In some embodiments the volume of the dosage form is about 0.37 ml and the solid unit dosage form comprises about 67.5 mg to about 200 mg pridopidine. In some embodiments the volume of the dosage form is about 0.37 ml and the solid unit dosage form comprises about 75 mg to about 100 mg pridopidine. In a further embodiment, the volume of the dosage form is 0.37 ml and the solid unit dosage form comprises 67.5 mg pridopidine. In an additional embodiment, the volume of the dosage form is 0.37 ml and the solid unit dosage form comprises 90 mg pridopidine. In another embodiment, the volume of the dosage form is 0.37 ml and the solid unit dosage form comprises 112.5 mg pridopidine. In a further embodiment, the volume of the dosage form is 0.37 ml and the solid unit dosage form comprises 125 mg pridopidine. In an additional embodiment, the volume of the dosage form is 0.37 ml and the solid unit dosage form comprises 135 mg pridopidine. In another embodiment, the volume of the dosage form is 0.37 ml and the solid unit dosage form comprises 150 mg pridopidine. In an additional embodiment, the volume of the dosage form is 0.37 ml and the solid unit dosage form comprises 175 mg pridopidine. In another embodiment, the volume of the dosage form is 0.37 ml and the solid unit dosage form comprises 150 mg pridopidine.

In some embodiments the volume of the dosage form is about 0.41 ml and the solid unit dosage form comprises about 125 mg to about 175 mg pridopidine. In a further embodiment, the volume of the dosage form is 0.41 ml and the solid unit dosage form comprises 125 mg pridopidine. In a further embodiment, the volume of the dosage form is 0.41 ml and the solid unit dosage form comprises 135 mg pridopidine. In an additional embodiment, the volume of the dosage form is 0.41 ml and the solid unit dosage form comprises 150 mg pridopidine. In a further embodiment, the volume of the dosage form is 0.41 ml and the solid unit dosage form comprises 175 mg pridopidine. In an additional embodiment, the volume of the dosage form is 0.41 ml and the solid unit dosage form comprises 180 mg pridopidine. In another embodiment, the volume of the dosage form is 0.41 ml and the solid unit dosage form comprises 200 mg pridopidine.

In some embodiments the volume of the dosage form is about 0.5 ml and the solid unit dosage form comprises about 90 mg to about 200 mg pridopidine. In a further embodiment, the volume of the dosage form is 0.5 ml and the solid unit dosage form comprises 90 mg pridopidine. In a further embodiment, the volume of the dosage form is 0.5 ml and the solid unit dosage form comprises 100 mg pridopidine. In a further embodiment, the volume of the dosage form is 0.5 ml and the solid unit dosage form comprises 112.5 mg pridopidine. In a further embodiment, the volume of the dosage form is 0.5 ml and the solid unit dosage form comprises 125 mg pridopidine. In an additional embodiment, the volume of the dosage form is 0.5 ml and the solid unit dosage form comprises 135 mg pridopidine. In another embodiment, the volume of the dosage form is 0.5 ml and the solid unit dosage form comprises 150 mg pridopidine. In a further embodiment, the volume of the dosage form is 0.5 ml and the solid unit dosage form comprises 175 mg pridopidine. In an additional embodiment, the volume of the dosage form is 0.5 ml and the solid unit dosage form comprises 180 mg pridopidine. In another embodiment, the volume of the dosage form is 0.5 ml and the solid unit dosage form comprises 200 mg pridopidine.

In some embodiments the volume of the dosage form is about 0.54 ml and the solid unit dosage form comprises about 150 mg to about 200 mg pridopidine. In a further embodiment, the volume of the dosage form is 0.54 ml and the solid unit dosage form comprises 150 mg pridopidine. In a further embodiment, the volume of the dosage form is 0.54 ml and the solid unit dosage form comprises 175 mg pridopidine. In a further embodiment, the volume of the dosage form is 0.54 ml and the solid unit dosage form comprises 180 mg pridopidine. In an additional embodiment, the volume of the dosage form is 0.54 ml and the solid unit dosage form comprises 200 mg pridopidine.

In one embodiment, the solid unit dosage form is in the form of a tablet or a soft gelatin capsule. In another embodiment, the solid unit dosage form is in the form of a tablet. In some embodiments, an overcoat layer completely surrounds the tablet. In further embodiments, solid unit dosage form is in the form of a capsule. In further embodiments, the solid unit dosage form is in the form of encapsulated mini-tablets. In some embodiments, the mini-tablets are coated. In some embodiments, the coating on the dosage form is an immediate release coating.

In one embodiment, the solid unit dosage form releases not less than (NLT) 80% of pridopidine within 30 minutes when the solid unit dosage form is tested in a dissolution apparatus as specified herein. In another embodiment, the solid unit dosage form releases 80-100%, 85-100%, 90-100%, 95-100% or about 98% of pridopidine within 30 minutes when the solid unit dosage form is tested in a dissolution apparatus as specified herein. In certain embodiments, the solid unit dosage form releases 80-100%, 85-100%, 90-100%, 95-100% or about 98% of pridopidine within 15 minutes when tested as specified herein.

For purposes of determining the dissolution rate or percentage release as expressed herein, the measurement is performed using a USP #2 dissolution apparatus comprising phosphate buffer pH 6.8 at 37° C.±0.5° C. as the dissolution medium, and a rotation speed of 50 revolutions per minute.

In certain embodiments, the solid unit dosage form releases NLT 80% of pridopidine within 30 minutes when tested in a USP #2 apparatus comprising phosphate buffer pH 6.8 at 37° C.+0.5° C., using a rotation speed of 50 revolutions per minute.

In preferred embodiments, the solid unit dosage form releases NLT 85% of pridopidine within 15 minutes when tested in a USP #2 apparatus comprising phosphate buffer pH 6.8 at 37° C.+0.5° C., using a rotation speed of 50 revolutions per minute.

Description of the USP apparatus and its use is available from the United States Pharmacopeia (USP). (USP <711> DISSOLUTION, 2016 hereby incorporated by reference in its entirety).

In one embodiment, the pharmaceutically acceptable excipient is selected from the group consisting of: filler, glidant, lubricant, disintegrant and mixtures thereof.

In one embodiment, the filler is selected from a group consisting of: microcrystalline cellulose, sugar spheres, lactose, sorbitol, dextrose, sucrose, mannitol, dibasic or tribasic calcium phosphate, calcium sulfate, starch, Retalac® (equal parts of hypromellose with milled alpha-lactose monohydrate grade) and mixtures thereof. In another embodiment, the filler is silicified microcrystalline cellulose.

In a further embodiment, the filler is between 10% and 80% by weight of the solid unit dosage form. In a further embodiment, the filler is between 15% and 80% by weight of the solid unit dosage form. In an additional embodiment, the filler is between 20% and 46% by weight of the solid unit dosage form. In an additional embodiment, the filler is between 26% and 46% by weight of the solid unit dosage form. In another embodiment, the filler is about 36% by weight of the solid unit dosage form. In another embodiment, the filler is about 40% by weight of the solid unit dosage form. In another embodiment, the filler is about 55% by weight of the solid unit dosage form. In some embodiments, the filler is between 50% and 70% by weight of the solid unit dosage form. In additional embodiments, the filler is about 60% by weight of the solid unit dosage form.

In one embodiment, the lubricant is selected from a group consisting of: sodium stearyl fumarate, stearic acid, magnesium stearate, calcium stearate, zinc stearate, talc, glyceryl behenate, glyceryl monostearate, and mixtures thereof. In another embodiment, the lubricant is magnesium stearate.

In one embodiment, the lubricant is present in an amount of about 0.5% to 2.0% by weight of the solid unit dosage form. In another embodiment, the lubricant is present in an amount of about 0.5% to 1.5% by weight of the solid unit dosage form. In some embodiments, the lubricant is present in an amount of about 0.8% to 1.0% by weight of the solid unit dosage form.

In some embodiments, the dosage form comprises granules and further comprises a disintegrant. Without wishing to be bound to theory, the disintegrant facilitates the immediate release of the API. In one embodiment, the disintegrant is a superdisintegrant. In another embodiment, the disintegrant is selected from the group consisting of: croscarmellose sodium, crospovidone, sodium starch glycolate, and polacrilin potassium.

In an embodiment, the disintegrant is present in an amount of about 1% to 10% by weight of the solid unit dosage form by weight of the solid unit dosage form. In an embodiment, the disintegrant is present in an amount of about 2° % to 10% by weight of the solid unit dosage form by weight of the solid unit dosage form. In an embodiment, the disintegrant is present in an amount of about 1.9% to 3.6% by weight of the solid unit dosage form. In an embodiment, the disintegrant is present in an amount of about 2.4% and 3.0% by weight of the solid unit dosage form. In an embodiment, the disintegrant is present in an amount of between 2% and 6% by weight of the solid unit dosage form. In an embodiment, the disintegrant is present in an amount of between 4% and 10% by weight of the solid unit dosage form. In an embodiment, the disintegrant is present in an amount of between 4% and 6% by weight of the solid unit dosage form. In another embodiment, the disintegrant is present in an amount of about 2.9% by weight of the solid unit dosage form. In another embodiment, the disintegrant is present in an amount of about 4% by weight of the solid unit dosage form. In another embodiment, the pridopidine is pridopidine base or pridopidine salt. In a further embodiment, the pridopidine is pridopidine hydrochloride.

In one embodiment, the solid unit dosage form is a size 2 capsule having a volume of 0.37 ml comprising 76.2 mg to 127 mg of pridopidine HCl. In some embodiments, the capsule is size 2 and comprises 76.2 mg of pridopidine hydrochloride (67.5 mg of pridopidine base), 125.8 mg of silicified microcrystalline cellulose, 6.0 mg of croscarmellose, and 2.0 mg of magnesium stearate. In another embodiment, the capsule is size 2 and comprises 101.6 mg of pridopidine hydrochloride (90 mg of pridopidine base), 125.8 mg of silicified microcrystalline cellulose, 6.0 mg of croscarmellose, and 2.0 mg of magnesium stearate. In a further embodiment, the capsule is size 2 and comprises 127.0 mg of pridopidine hydrochloride (112.5 mg of pridopidine base), 75.0 mg of silicified microcrystalline cellulose, 6.0 mg of croscarmellose, and 2.0 mg of magnesium stearate.

In a further embodiment, the capsule is size 2 and comprises 85 mg of pridopidine hydrochloride (75 mg of pridopidine base), 105 mg of silicified microcrystalline cellulose, 8.0 mg of croscarmellose and 2.0 mg of magnesium stearate.

In a further embodiment, the capsule is size 2 and comprises 113 mg of pridopidine hydrochloride (100 mg of pridopidine base), 77.0 mg of silicified microcrystalline cellulose, 8 mg of croscarmellose and 2.0 mg of magnesium stearate.

In a further embodiment, the capsule is size 2 and comprises 170 mg of pridopidine hydrochloride (150 mg of pridopidine base), 20.5 mg of silicified microcrystalline cellulose, 8.0 mg of croscarmellose, and 2.0 mg of magnesium stearate.

In an embodiment of the solid unit dosage, the capsule is size 2 and comprises between 40% to 85% w/w of pridopidine salt, between 10% to 80% w/w a filler, and between 1% to 10% w/w a disintegrant. In an embodiment of the solid unit dosage, the capsule is size 2 and comprises between 50% to 85% w/w of pridopidine salt, between 10% to 80% w/w a filler, and between 1% to 10% w/w a disintegrant. In another embodiment, the pridopidine salt is pridopidine HCl.

In an embodiment of the above solid unit dosage forms, the capsule parameters are presented in Chart 1, hereinbelow.

The invention also provides a solid unit dosage form comprising granules. The invention also provides a solid unit dosage form comprising mini-tablets. The solid unit dosage form may be administered once, twice or thrice daily, as recommended, for example, by the attending physician. The invention further provides a method of treating a subject afflicted with a condition selected from Huntington's Disease, Parkinson's disease, iatrogenic and non-iatrogenic Parkinsonism, dyskinesias such as drug induced-dyskinesias including LID-induced dyskinesias, dystonias, Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease and Retts syndrome, wherein the method comprises administering the solid unit dosage form of the invention to the subject in need thereof. In some embodiments, the dosage form comprises mini-tablets. In some embodiments, the mini-tablets are encapsulated. In some, the mini-tablets are coated. The coated mini-tablets may be administered to the subject dispersed for example in a soft food, for example in a fruit sauce or mashed vegetables.

The invention additionally provides a method of treating an individual afflicted with a neurodegenerative disease or a disease related to dopamine, comprising once daily administration of a solid unit dosage form of the invention.

The invention also provides a solid unit dosage form as described herein, for use in the treatment of Huntington's Disease, Parkinson's disease, iatrogenic and non-iatrogenic parkinsonism, dyskinesias such as drug induced-dyskinesias including LID-induced dyskinesias, dystonias, Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease or Retts syndrome.

The invention further provides for the use of a solid unit dosage form as described herein, for the manufacture of a medicament for treating a subject afflicted with Huntington's Disease, Parkinson's disease, iatrogenic and non-iatrogenic Parkinsonism, dyskinesias such as drug induced-dyskinesias including LID-induced dyskinesias, dystonias. Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease or Retts syndrome.

Additionally, the invention provides a package comprising:

a solid unit dosage form as described herein; and instructions for use of the solid unit dosage form to treat or delay disease progression in a subject afflicted with Huntington's Disease, Parkinson's disease, iatrogenic and non-iatrogenic parkinsonism, dyskinesias such as drug induced-dyskinesias including LID-induced dyskinesias, dystonias, Tourette's disease, iatrogenic and non-iatrogenic psychoses and hallucinoses, schizophrenia disorder or schizophreniform disorder, mood and anxiety disorders, manodepressive illness, depression, obsessive-compulsive disease, a sleep disorder, autism spectrum disorder, ADHD, age-related cognitive impairment, abuse of alcohol and substances used as narcotics, Alzheimer's disease or Retts syndrome.

Also provided herein is a process for preparing granules, the process comprising forming a wet granulate or a dry granulate. In preferred embodiments, the process comprises forming a wet granulate. In one embodiment, the process further comprises mixing pridopidine with a solution of water and/or an organic solution, with or without a binder, to form a wet granulate. In another embodiment, the process further comprises mixing pridopidine with one or more intragranular excipients, and a solution of water and/or an organic solution, with or without a binder, to form a wet granulate. In some embodiments, the intragranular excipient is a filler, a disintegrant or a combination thereof. In some embodiments, the intragranular excipient is disintegrant. In preferred embodiments, the intragranular excipient comprises disintegrant and filler. Intragranular excipient refers to an excipient that forms a part of the granules. In some embodiments, one or more extragranular excipients are present in the dosage form. In some embodiments the dosage form is mini-tablets. In some embodiments an extragranular disintegrant is present in the dosage form in an amount of about 0-4% of the total weight of the dosage form. In some embodiments, the total amount of the extragranular and intragranular disintegrants is about 1.9% to about 7.6% of the total weight of the dosage form. In some embodiments, the total amount of the disintegrant is about 1% to about 10% of the total weight of the dosage form.

In some embodiments, the average particle size of the pridopidine or pridopidine salt following the wet granulation process include less than 75 micron (pan) and up to 430 microns.

Figure 4:
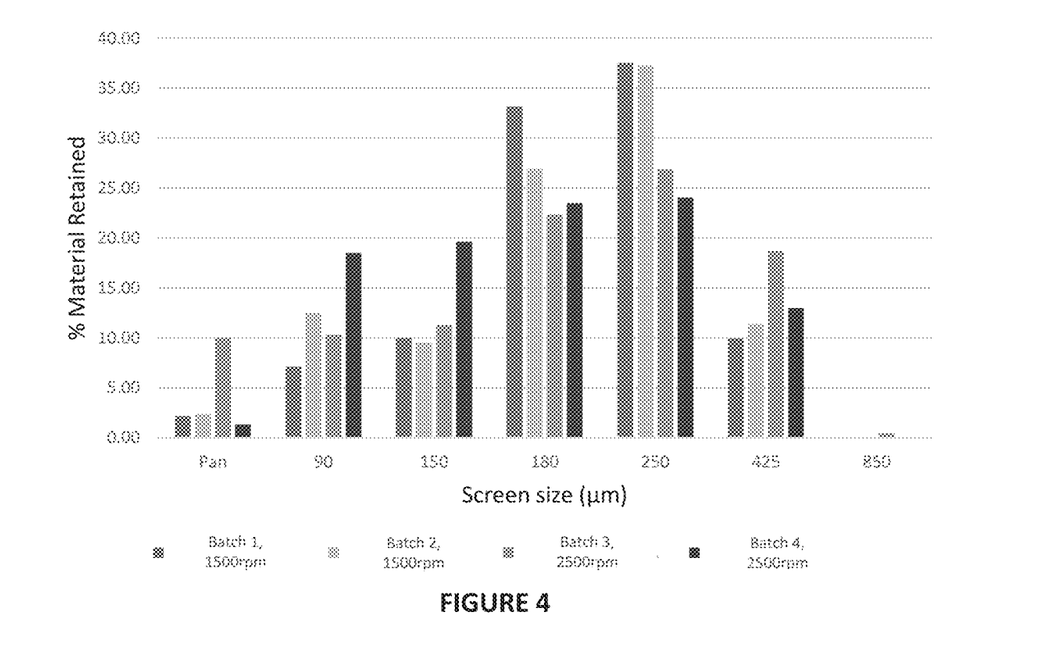
FIG. 4 is a sieve analysis of the granulate prepared by wet granulation process. The granules were milled in a laboratory scale Quadro Comil. Batch 1 and 2 were milled at 1500 rpm speed. Batch 3 and 4 were milled at 2500 rpm speed. The particle size distribution was observed indicating similar particles size distribution profile in the range from Pan (from less than 75 micron) to 425 micron.

In another embodiment, the particle size distribution is as presented in FIG. 4.

The solid unit dosage form may comprise the granules as described herein.

In an embodiment, the ratio of the amount of pridopidine to the volume is 135-500 mg/ml, 135-400 mg/ml, 135-370 mg/ml, 175-600 mg/ml, 175-500 mg/ml, 175-400 mg/ml, 175-370 mg/ml, 200-600 mg/ml, 200-500 mg/ml, 200-400 mg/ml, 200-370 mg/ml, 240-600 mg/ml, 240-500 mg/ml, 240-400 mg/ml, or 240-370 mg/ml. In another embodiment, the ratio of the amount of pridopidine to the volume of the dosage form is about 135 mg/ml, about 140 mg/ml, about 150 mg/ml about 160 mg/ml, about 170 mg/ml about 180 mg/ml, about 190 mg/ml, about 200 mg/ml, about 210 mg/ml, about 220 mg/ml, about 230 mg/ml, about 240 mg/ml, about 250 mg/ml, about 260 mg/ml, about 270 mg/ml, about 280 mg/ml, about 290 mg/ml, about 300 mg/ml, about 310 mg/ml, about 320, about 330 mg/ml, about 340 mg/ml, about 350 mg/ml, about 360 mg/ml about 370 mg/ml, about 380 mg/ml, about 390 mg/ml or about 400 mg/ml.

In one embodiment, the volume of the dosage form is about 0.37 ml and the solid unit dosage form comprises 67.5-200 mg pridopidine base, or equivalent pridopidine salt, for example pridopidine HCl. In another embodiment, the volume of the dosage form is about 0.30 ml and the solid unit dosage form comprises 67.5-180 mg pridopidine. In one embodiment, the volume of the dosage form is about 0.5 ml and the solid unit dosage form comprises about 90 mg to about 200 mg pridopidine. In a further embodiment, the volume of the dosage form is about 0.21 ml and the solid unit dosage form comprises 67.5-135 mg pridopidine. In an additional embodiment, the volume of the dosage form is about 0.13 ml and the solid unit dosage form comprises 67.5 mg pridopidine. In another embodiment, the volume of the dosage form is about 0.37 ml and the solid unit dosage form comprises 67.5-112.5 mg pridopidine.

In another embodiment, the volume of the dosage form is about 0.37 ml and the solid unit dosage form comprises 67.5 mg pridopidine. In a further embodiment, the volume of the dosage form is about 0.37 ml and the solid unit dosage form comprises 90 mg pridopidine. In a further embodiment, the volume of the dosage form is about 0.37 ml and the solid unit dosage form comprises 112.5 mg pridopidine.

In some embodiments, the dosage form is a capsule. In some embodiments, the capsule is size 1 and the solid unit dosage form comprises 67.5-200 mg pridopidine. In an embodiment, the capsule is size 2 and the solid unit dosage form comprises 67.5-200 mg pridopidine. In another embodiment, the capsule is size 3 and the solid unit dosage form comprises 67.5-180 mg pridopidine. In a further embodiment, the capsule is size 4 and the solid unit dosage form comprises 67.5-135 mg pridopidine. In an additional embodiment, the capsule is size 5 and the solid unit dosage form comprises 67.5 mg pridopidine. In one embodiment, the capsule is size 2 and the solid unit dosage form comprises 67.5 mg of pridopidine, 75 mg of pridopidine, 90 mg of pridopidine, 100 mg pridopidine or 112.5 mg of pridopidine. In one embodiment, the capsule is size 2 and the solid unit dosage form comprises 67.5 mg of pridopidine. In another embodiment, the capsule is size 2 and the solid unit dosage form comprises 75 mg of pridopidine. In another embodiment, the capsule is size 2 and the solid unit dosage form comprises 90 mg of pridopidine. In another embodiment, the capsule is size 2 and the solid unit dosage form comprises 100 mg of pridopidine. In another embodiment, the capsule is size 2 and the solid unit dosage form comprises 112.5 mg of pridopidine.

In another embodiment, the dosage form comprises pridopidine HCl at about 35-85% by weight of the solid unit dosage form. In one embodiment, the solid unit dosage form comprises pridopidine HCl at about 36-85%, 40-85%, 45-85%, 50-85%, or 42-85% by weight of the solid unit dosage form In one embodiment, the capsule is size 2 and comprises 36.3% pridopidine HCl by weight (32.1% of pridopidine base by weight), 59.9% silicified microcrystalline cellulose by weight, 2.9% croscarmellose by weight, and 1.0% magnesium stearate by weight. In another embodiment, the capsule is size 2 and comprises 60.5% pridopidine HCl by weight (53.6% pridopidine base by weight), 35.7% silicified microcrystalline cellulose by weight, 2.9% croscarmellose by weight, and 1.0% magnesium stearate by weight.

In one embodiment, the capsule is size 2 and comprises 42% pridopidine HCl by weight, 53% silicified microcrystalline cellulose by weight, 4% croscarmellose by weight, and 1.0% magnesium stearate by weight. In another embodiment, the capsule is size 2 and comprises 57% pridopidine HCl by weight, 39% silicified microcrystalline cellulose by weight, 4% croscarmellose by weight, and 1.0% magnesium stearate by weight. In another embodiment, the capsule is size 2 and comprises 85% pridopidine HCl by weight, 10% silicified microcrystalline cellulose by weight, 4% croscarmellose by weight, and 1.0% magnesium stearate by weight.

In some embodiments, the dosage forms comprise pridopidine base. In some embodiments, the dosage forms comprise pridopidine HCl. The factor for converting mass of pridopidine HCl to mass of pridopidine base is 0.885.

In any of the foregoing embodiments, the dosage form comprises pridopidine as pridopidine base or the equivalent amount of pridopidine as pridopidine salt, for example pridopidine HCl.

In further embodiments, the solid unit dosage form has the composition and capsule size of any one of the specific examples listed in Table 9, Table 10, Table 11, or Table 12.

In any of the foregoing embodiments, granules may be used instead of a solid unit dosage form. In any of the foregoing embodiments, the dosage form comprises mini-tablets. In some embodiments, the mini-tablets are encapsulated. In some embodiments the mini-tablets are coated. In some embodiments the mini-tablets are not coated.

For the foregoing embodiments, each embodiment disclosed herein is contemplated as being applicable to each of the other disclosed embodiments. In addition, the elements recited in solid unit dosage form embodiments can be used in the method, use and package embodiments described herein.

Terms

As used herein, and unless stated otherwise, each of the following terms shall have the definition set forth below.

As used herein, the term "Cmax" refers to the maximum plasma, serum or blood concentration of a drug, following administration of the drug, e.g. pridopidine, or a pharmaceutically acceptable salt thereof.

As used herein, the term "Cmin" refers to the minimum plasma, serum or blood concentration of a drug, following administration of the drug, e.g. pridopidine, or a pharmaceutically acceptable salt thereof.

As used herein, the term "Tmax" refers to the time required to reach the maximal plasma, serum or blood concentration ("Cmax") of the drug, following administration of the drug, e.g. pridopidine, or a pharmaceutically acceptable salt thereof.

As used herein, the term "AUC" refers to the area under the plasma, serum or blood concentration versus time curve. "$AUC_{0-t}$," refers to the area under the plasma, serum or blood concentration versus time curve wherein t (hours) is the last measured time point, for example $AUC_{0-24}$, refers to area under the curve from time of administration for 24 hours. "$AUC_{infinity}$," refers to the area under the plasma, serum or blood concentration versus time curve extrapolated to infinity. $AUC_{24,ss}$ refers to area under the concentration-time curve from 0 to 24 hours at steady state As used herein, "pridopidine" means pridopidine base or a pharmaceutically acceptable salt thereof, as well as derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, hereby incorporated by reference in their entireties. In certain embodiments, pridopidine is a pharmaceutically acceptable salt, such as the HCl salt or tartrate salt. Preferably, in any embodiments of the invention as described herein, the pridopidine is in the form of its hydrochloride salt.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

In some embodiments, the dosage forms include deuterated pridopidine.

"Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%%, for example 50%, 60%, 70%, 75%, 80%, 85%, 90%, 95%, 98% or 100%. Deuterium-enriched compounds may be obtained by exchanging hydrogen with deuterium or synthesizing the compound with deuterium-enriched starting materials The solid oral dosage form of the present invention is suitable for administration in a one unit dosage form. The pharmaceutical composition of the invention may be administered by any convenient route, which suits the desired therapy. Oral dosage forms for the purpose of the present invention include capsules, tablets, pellets, granules, powders coated or uncoated and combinations thereof. Optionally, if the dosage form is a capsule, the pridopidine is provided in the form of coated or uncoated pellets, granules, powders, mini tablets, tablets or capsules.

Further details on techniques for formulation and administration may be found in the latest edition of Remington's Pharmaceutical Sciences (Maack Publishing Co., Easton, Pa.).

Tablets may contain suitable binders, glidants, lubricants, disintegrating agents, coloring agents, flavoring agents, flow-inducing agents, melting agents, and plasticizers. For instance, for oral administration in the dosage unit form of a tablet or capsule, the active drug component can be combined with an oral, non-toxic, pharmaceutically acceptable, inert carrier such as xylose, gelatin, agar, starch, methyl cellulose, dicalcium phosphate, calcium sulfate, mannitol, sorbitol, microcrystalline cellulose and the like. Suitable binders include starch, gelatin, natural sugars such as corn starch, natural and synthetic gums such as acacia, tragacanth, or sodium alginate, povidone, polyvidone, carboxymethylcellulose, hydroxypropyl cellulose, polyethylene glycol, waxes, and the like. Glidants used in these dosage forms include silicon dioxide and the like. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

The dosage forms of the present invention may further comprise one or more pharmaceutically acceptable carriers or excipients.

Examples of pharmaceutical acceptable excipients are fillers, binders, glidants, plasticizer and lubricants.

Compression can be accomplished using conventional equipment. Compaction—typically, the blend of active ingredients with or without excipients is passed through a roller apparatus. However, other means for compacting the API (Active Pharmaceutical Ingredient) mixture, e.g., compaction into slugs (or "slugging"), may be used.

As used herein, the term "immediate release" or "IR" refers to a dosage form that releases not less than (NLT) 80% of the active pharmaceutical ingredient within 30 minutes when tested in a USP #2 dissolution apparatus comprising phosphate buffer pH 6.8 at 37° C.+0.5° C., using a rotation speed of 50 revolutions per minute, as specified herein.

Pridopidine base and pridopidine HCl have similar dissolution rates when tested under these conditions. In a preferred embodiment, the solid unit dosage form releases NLT 85% of pridopidine within 15 minutes when tested as specified herein. As used herein, a slower dissolution profile is one in which the escape or release of a drug from the dosage form is slower, i.e. it takes more time for the drug to be released in a slower dissolution profile than a faster dissolution profile. A "salt" is salt of the instant compounds which have been modified by making acid or base salts of the compounds. The term "pharmaceutically acceptable salt" in this respect, refers to the relatively non-toxic, inorganic and organic acid or base addition salts of compounds of the present invention. It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

As used herein, to "treat" or "treating" encompasses attenuating a symptom, inducing inhibition, regression, or stasis of a disorder and/or disease. As used herein, "inhibition" of disease progression or disease complication in a subject means preventing or reducing the disease progression and/or disease complication in the subject. In one embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Subject" includes humans. The terms "human," "patient" and "subject" are used interchangeably herein in particular embodiments; the subject is a human adult or a human adult having a mass of 70 kg. In some embodiments, the subject is a human child or human adolescent. As used herein, "effective" means the quantity of a compound that is sufficient to yield an indicated therapeutic response when used in the manner of this disclosure. For example, an amount effective to treat a movement disorder. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives. In a preferred embodiment, administration of an effective amount of a therapeutic compound is without undue adverse side effects (such as toxicity, irritation, or allergic response), commensurate with a reasonable benefit/risk ratio when used in the manner of this disclosure.

As used herein, an "amount" or "dose" of pridopidine as measured in milligrams refers to the milligrams of underivatized pridopidine base present in a preparation, regardless of the form of the preparation. A dosage of "90 mg pridopidine" means the amount of pridopidine in a preparation is sufficient to provide 90 mg of underivatized pridopidine base having a naturally occurring isotope distribution, regardless of the form of the preparation. Thus, when in the form of a salt, e.g. a pridopidine hydrochloride salt, the weight of the salt form necessary to provide a dose of 90 mg pridopidine would be greater than pridopidine mg due to the presence of the salt ion. However, if an amount of "pridopidine HCl" or "pridopidine hydrochloride" is listed, this refers to the amount of the salt, i.e. pridopidine hydrochloride, and not pridopidine base. Similarly, when in the form of a deuterium-enriched derivative, the mass of the derivatized form necessary to provide a dose of 90 mg underivatized pridopidine base having a naturally occurring isotope distribution would be greater than 90 mg due to the presence of the additional deuterium.

As used herein, a "unit dose", "unit doses" and "unit dosage form(s)" or "solid unit dosage form" mean a single drug administration entity/entities, for example tablets including mini-tablets, and capsules. The mini-tablets may be, for example, enclosed in a capsule or presented in a sachet.

As used herein, "about" in the context of a numerical value or range means 10% of the numerical value or range recited or claimed.

As used herein, the term "once daily" means administering a dose once every 24 hours. As used herein, the term "QD" or "qd" refers to a once daily administration. "bid" or "b.i.d." refers to twice daily administration, and "tid" or "t.i.d." refers to thrice daily administration.

As used herein, reference to a total weight of a dosage form refers to the total weight of a tablet (including any finishing coat), and in the case of a capsule, refers to the total weight of the capsule contents, excluding the weight of the capsule itself.

As used herein, reference to a volume of a solid unit dosage form refers to the volume of a solid unit dosage form excluding any finishing coat. In the case of a tablet, the volume refers to the volume of the tablet and excludes any finishing coat. In the case of a capsule, the volume refers to the internal volume of the closed capsule, excluding the volume of the capsule itself.

As used herein, the term "bioavailability" refers to the rate and extent to which an active pharmaceutical ingredient is absorbed from a capsule or dosage form and becomes available at the site of action.

Approximate capsule size and volume are defined in Chart 1, below.

Chart 1: Size and Volume of Commercially Available Capsule Shells

| Capsule Size | Outer Diameter (mm) (cap) | Overall closed length (mm) | Capsule Volume (ml) |
|---|---|---|---|
| 0 | 7.64 | 21.7 | 0.68 |
| 1 | 6.91 | 20.4 | 0.54 |
| elongated (el) 1 | 6.91 | 19.4 | 0.48-0.50 |
| 2 | 6.36 | 19.3 | 0.41 |
| elongated (el) 2 | 6.35 | 17.6-18.0 | 0.36-0.37 |
| 3 | 5.82 | 15.7-15.9 | 0.27-0.30 |
| 4 | 5.32 | 14.3 | 0.20-0.21 |
| 5 | 4.91 | 11.1 | 0.13 |

As used herein, the "closed length" of a capsule is the length of a closed capsule on its longest axis.

Any known superdisintegrant may be used in this invention. Examples of superdisintegrants include, but are not limited to crospovidone, croscarmellose sodium, sodium starch glycolate, and polacrilin potassium. In some embodiments the superdisintegrant is croscarmellose sodium, for example brand Ac-Di-Sol®. Examples of superdisintegrants may be found in Mangal 2012 and Mohanachandran 2011, hereby incorporated by reference in their entireties.

Silicified microcrystalline cellulose may be any commercially available form of this excipient, for example Prosolv® SMCC 90.

The following numbered clauses define various aspects and features of the present invention 1. A solid unit dosage form comprising a therapeutically effective amount of pridopidine and at least one pharmaceutically acceptable excipient, wherein the dosage form has a volume and wherein the ratio of the amount of pridopidine to the volume of the dosage form is 135-600 mg/ml.
2. The solid unit dosage form of clause 1, wherein the ratio of the amount of pridopidine to the volume of the dosage form is 135-500 mg/ml or 175-370 mg/ml.
3. The solid unit dosage form of any one of clauses 1-2 wherein the solid unit dosage form comprises about 67.5 mg, about 90 mg, about 100 mg, about 112.5 mg, about 125 mg, about 135 mg, about 150 mg, or about 180 mg of pridopidine.
4. The solid unit dosage form of clause 1 wherein:
a) the volume of the dosage form is 0.37 ml and the solid unit dosage form comprises 67.5-200 mg pridopidine;

b) the volume of the dosage form is 0.30 ml and the solid unit dosage form comprises 67.5-180 mg pridopidine;

c) the volume of the dosage form is 0.21 ml and the solid unit dosage form comprises 67.5-135 mg pridopidine; or d) the volume of the dosage form is 0.13 ml and the solid unit dosage form comprises 67.5 mg pridopidine.

5. The solid unit dosage form of any one of clauses 1-4, wherein the solid unit dosage form comprises 67.5 mg of pridopidine, 75 mg of pridopidine, 90 mg of pridopidine, 100 mg of pridopidine, 125 mg of pridopidine, 150 mg of pridopidine, 175 mg of pridopidine or 200 mg of pridopidine.

6. The solid unit dosage form of clause 1 or 2, wherein the solid unit dosage form comprises 75 mg or 100 mg or 150 mg of pridopidine.

7. The solid unit dosage form of clause 1 wherein the volume of the dosage form is 0.37 ml and the solid unit dosage form comprises 67.5, 75 or 100 mg pridopidine.

8. The solid unit dosage form of clause 1 wherein the volume of the dosage form is 0.37 ml and the solid unit dosage form comprises 90 mg pridopidine 9. The solid unit dosage form of clause 1 wherein the volume of the dosage form is 0.37 ml and the solid unit dosage form comprises 112.5 mg pridopidine.

10. The solid unit dosage form of any one of clauses 1-9, wherein the solid unit dosage form is in the form of a tablet or a soft gelatin capsule.

11. The solid unit dosage form of clause 10, wherein the solid unit dosage form is in the form of a tablet.

12. The tablet of clause 11, wherein an overcoat layer completely surrounds the tablet.

13. The solid unit dosage form of clause 10, wherein the solid unit dosage form is in the form of a capsule.

14. The solid unit dosage form of any one of clauses 1-13, wherein the solid unit dosage form releases 80-100% of pridopidine after 10 minutes when the solid unit dosage form is placed in an apparatus comprising a dissolution medium.

15. The solid unit dosage form of clause 14, wherein the solid unit dosage form releases 85-100%, 90-100%, 95-100% or about 98% of pridopidine after 10 minutes when the solid unit dosage form is placed in an apparatus comprising a dissolution medium.

16. The solid unit dosage form of clause 14 or 15, wherein the dissolution medium is HCl 0.1N, water, acetate buffer pH 4.5 or phosphate buffer pH 6.8.

17. The solid unit dosage form of any one of clauses 15 or 16, wherein the apparatus is a basket dissolution apparatus or a paddle with at least one sinker maintained at a temperature of 37° C. rotating at 50 to 100 revolutions per minute.

18. The solid unit dosage form of any one of clauses 1-17, wherein the pharmaceutically acceptable excipient is selected from the group consisting of: filler, glidant, lubricant, disintegrant and mixtures thereof.

19. The solid unit dosage form of clause 18, wherein the filler is selected from a group consisting of: microcrystalline cellulose, sugar spheres, lactose, sorbitol, dextrose, sucrose, mannitol, dibasic or tribasic calcium phosphate, calcium sulfate, starch, retalac and mixtures thereof.

20. The solid unit dosage form of clause 19, wherein the filler is silicified microcrystalline cellulose.

21. The solid unit dosage form of any one of clauses 18-20, wherein the filler is between 10% and 80% by weight of the solid unit dosage form.

22. The solid unit dosage form of any one of clauses 18-20, wherein the filler is between 10% and 60% by weight of the solid unit dosage form.

23. The solid unit dosage form of clause 22, wherein the filler is about 40% by weight of the solid unit dosage form.

24. The solid unit dosage form of any one of clauses 18-20, wherein the filler is between 50% and 70%, by weight of the solid unit dosage form.

25. The solid unit dosage form of any one of clauses 18-20, wherein the filler is about 55% by weight of the solid unit dosage form.

26. The solid unit dosage form of any one of clauses 18-25, wherein the lubricant is selected from a group consisting of: sodium stearyl fumarate, stearic acid, magnesium stearate, calcium stearate, zinc stearate, talc, glyceryl behenate, glyceryl monostearate, and mixtures thereof.

27. The solid unit dosage form of clause 26, wherein the lubricant is magnesium stearate.

28. The solid unit dosage form of any one of clauses 18-27, wherein the lubricant is between 0.5% and 2.0% by weight of the solid unit dosage form.

29. The solid unit dosage form of any one of clauses 18-28, wherein the lubricant is between 0.5% and 1.5% by weight of the solid unit dosage form.

30. The solid unit dosage form of clause 29, wherein the lubricant is about 1.0% by weight of the solid unit dosage form.

31. The solid unit dosage form of any one of clause 18-30, wherein the disintegrant is a superdisintegrant.

32. The solid unit dosage form of any one of clause 18-30, wherein the disintegrant is selected from the group consisting of: croscarmellose sodium, crospovidone, sodium starch glycolate, and polacrilin potassium.

33. The solid unit dosage form of any one of clauses 18-32, wherein the disintegrant is between 1.9% and 10% by weight of the solid unit dosage form.

34. The solid unit dosage form of clause 33, wherein the disintegrant is about 2.9% or 4% by weight of the solid unit dosage form.

35. The solid unit dosage form according to any one of clauses 1-34, wherein the pridopidine is pridopidine base or pridopidine salt.

36. The solid unit dosage form according to any one of clauses 1-34, wherein the pridopidine is pridopidine hydrochloride.

37. The solid unit dosage form according to clause 13, wherein the capsule is size 2 and comprises 76.2 mg of pridopidine hydrochloride (67.5 mg of pridopidine base), 125.8 mg of silicified microcrystalline cellulose, 6.0 mg of croscarmellose, and 2.0 mg of magnesium stearate.

38. The solid unit dosage form according to clause 13, wherein the capsule is size 2 and comprises 101.6 mg of pridopidine hydrochloride (90 mg of pridopidine base), 125.8 mg of silicified microcrystalline cellulose, 6.0 mg of croscarmellose, and 2.0 mg of magnesium stearate.

39. The solid unit dosage form according to clause 13, wherein the capsule is size 2 and comprises 127.0 mg of pridopidine hydrochloride (112.5 mg of pridopidine base), 75.0 mg of silicified microcrystalline cellulose, 6.0 mg of croscarmellose, and 2.0 mg of magnesium stearate.

40. The solid unit dosage form of any one of clauses 1-39 comprising granules.

41. The solid unit dosage form of any one of clauses 1-40, wherein the solid unit dosage form is adapted for twice daily administration.

42. A method of treating a subject afflicted with a condition selected from Huntington's Disease, Parkinson's disease, iatrogenic and non-iatrogenic Parkinsonism, dyskinesias, dystonias, Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease and Retts syndrome, wherein the method comprises administering the solid unit dosage form of any of clauses 1-41 to the subject in need thereof.

43. A method of treating an individual afflicted with a neurodegenerative disease or a disease related to dopamine, comprising once daily administration of the solid unit dosage form of any one of clauses 1-41.

44. A solid unit dosage form according to any one of clauses 1-41, for use in the treatment of Huntington's Disease, Parkinson's disease, iatrogenic and non-iatrogenic Parkinsonism, dyskinesias, dystonias, Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease or Retts syndrome.

45. Use of a solid unit dosage form according to any one of clauses 1-41, for the manufacture of a medicament for treating a subject afflicted with Huntington's Disease, Parkinson's disease, iatrogenic and non-iatrogenic Parkinsonism, dyskinesias, dystonias. Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease or Retts syndrome.

46. A package comprising:
a) the solid unit dosage form of any one of clauses 1-41; and
b) instructions for use of the solid unit dosage form to treat or delay disease progression in a subject afflicted with Huntington's Disease, Parkinson's disease, iatrogenic and non-iatrogenic Parkinsonism, dyskinesias, dystonias, Tourette's disease, iatrogenic and non-iatrogenic psychoses and hallucinoses, schizophrenia disorder or schizophreniform disorder, mood and anxiety disorders, manodepressive illness, depression, obsessive-compulsive disease, a sleep disorder, autism spectrum disorder, ADHD, age-related cognitive impairment, abuse of alcohol and substances used as narcotics, Alzheimer's disease or Retts syndrome.

47. A process for preparing the granules of clause 40, the process comprising forming a wet granulate or a dry granulate.

48. The process of clause 47 further comprising mixing pridopidine with a solution of water and/or an organic solution, with or without a binder, to form a wet granulate.

49. The process of clause 47 or 48 further comprising mixing pridopidine with one or more intragranular excipients, and a solution of water and/or an organic solution, with or without a binder, to form a wet granulate.

50. The process of clause 49, wherein the intragranular excipient is a filler, a disintegrant or a combination thereof.

The solid unit dosage form of any one of clauses 1-41 comprising the granules of any one of clauses 47-49.

Throughout this application, various publications are referred to by first author and year of publication. Full citations for these publications are presented in a References section immediately before the claims. Disclosures of the documents and publications cited and those in the References section are hereby incorporated by reference in their entireties into this application in order to more fully describe the state of the art as of the date of the invention described herein.

The present invention is illustrated by the following examples, which are not intended to limit the scope of the invention. It will be appreciated that various modifications are within the spirit and scope of the invention.

EXAMPLES

Example 1: Dissolution Assays

USP #1 dissolution apparatus (basket) and USP #2 dissolution apparatus (paddle) are described in the United States Pharmacopeia, 29th Edition, chapter 711.

The dosage forms were tested in 0.1N HCl, acetate buffer pH4.5, and/or phosphate buffer pH 6.8 as presented in Table 1, below.

TABLE 1

| Dissolution parameters | |
|---|---|
| Drug product | Pridopidine dry mix and wet granulation capsules |
| Equipment | 6-vessel assembly, USP Apparatus #2 (paddle) equipped with sinkers |
| Dissolution media | 0.1N HCl Acetate buffer pH 4.5 <USP> Phosphate buffer pH 6.8 <USP> |
| Volume | 500 mL |
| Stirring rate | 50 rpm |
| Temperature | 37° C. ± 0.5° C. |
| Sampling time | 10, 15, 20 and 30 min. |

The samples at low pH were neutralized by the addition of 0.4N NaOH solution prior to the HPLC injection. The final concentration of pridopidine in the sample was calculated using a dilution factor. The percent dissolution of pridopidine, at each of the dissolution time points, was determined using calibrated reversed-phase high-performance liquid chromatography (RP-HPLC) with UV detection set at 268 nm.

The dosage forms exhibited a similar dissolution profile in all three solutions.

Example 2: Pridopidine Immediate Release Low Dose Capsules

The 22.5 mg and 45 mg dose formulations of immediate release capsules of pridopidine that were used in clinical studies (i.e. MermaiHD, HART, MAD, PRIDE-HD) are shown in Table 1. No other dosage form was prepared for the trials. The solid dosage forms contained 22.5 mg (Batch A), and 45 mg (Batch B) of pridopidine and the capsule size used for each dosage form is indicated in Table 2. These formulations were manufactured by dry mix of active material (pridopidine HCl) with filler and lubricant.

TABLE 2

Composition of Pridopidine IR Low Dose Dosage Form

| | | Formulation | |
|---|---|---|---|
| | Use | A (22.5 mg) | B (45 mg) |
| | | Composition mg/capsule | |
| Pridopidine HCl | API | 25.4 | 50.8 |
| Silicified Micro-crystalline Cellulose (Prosolv ® SMCC 90) | Filler | 43.2 | 86.4 |
| Magnesium Stearate | Lubricant | 1.4 | 2.8 |
| Total | | 70.0 | 140.0 |
| Capsule Size | | 4 | 2 |
| Capsule Color | | White | White |

A size 4 capsule was filled with the 70 mg final blend (Formulation A). A size 2 capsule was filled with the 140 mg final blend (Formulation B).

The dissolution profiles of the 22.5 mg formulation (Formulation A) and 45 mg formulation (Formulation B) show that the percentage of drug released is greater than or equal to 80% after 30 minutes as shown in Table 3.

TABLE 3

Dissolution Rate of Low Dose IR Compositions of Pridopidine in Phosphate buffer pH6.8

| | % Dissolution (Drug Release %)* | | | | |
|---|---|---|---|---|---|
| Time (min) | 0 | 10 | 15 | 20 | 30 |
| Formulation A | 0 | 87 | 93 | 98 | 99 |
| Formulation B | 0 | 58 | 80 | 92 | 96 |

*±5%

Example 3: Preliminary Pridopidine Immediate Release High Dose Capsules

A 67.5 mg pridopidine dosage form (Batch C) was made in order to test filling capsules with a high dose dry mix formulation. The 210 mg of blend (Batch C) did not fit into the capsule size 2 and was encapsulated in capsule size 1 elongated (1 el) due to the high bulk density of the blend (Table 4).

TABLE 4

Composition of Pridopidine IR High Dose Dosage Form

| | | Formulation |
|---|---|---|
| | Use | C (67.5 mg) Composition mg/capsule |
| Pridopidine HCl | API | 76.2 |
| Silicified Micro-crystalline Cellulose (Prosolv ® SMCC 90) | Filler | 129.6 |
| Magnesium Stearate | Lubricant | 4.2 |
| Total | | 210.0 |
| Capsule Size | | 1 elongated (el) |
| Capsule Color | | White |

Due to the high bulk density of the 67.5 mg blend and the need for high dose dosage forms in a suitable size capsule, two high dose pseudo proportional formulations were prepared using wet granulation technology: Formulation D, which contained 67.5 mg of pridopidine, and Formulation E, which contained 112.5 mg of pridopidine. These formulations were encapsulated in immediate release size 2 capsules. Wet granulation has many advantages including dust free formulations, improved flowability and elimination of poor content uniformity. The use of wet granulation allowed a high dose of pridopidine to be encapsulated in a smaller sized capsule. This process solved the blend uniformity and bulk problems associated with dry blend technology and enabled filing into smaller capsule shells for ease in handling and swallowing by patients afflicted with for example, neurodegenerative disorders, dysphagia and/or movement disorders.

The active material, pridopidine hydrochloride, was mixed in a high shear mixer with filler, silicified microcrystalline cellulose, and water. The wet granulate was dried, milled by conical milling equipment available from Quadro® Comil®, and then divided into 2 portions. Magnesium stearate was added as lubricant and silicified microcrystalline cellulose was added as filler to Formulations D and E, as shown in Table 4. Formulation D contained 67.5 mg of pridopidine and Formulation E contained 112.5 mg of pridopidine. Size 2 capsules were filled with the final blends, see Table 5. The method worked equally well for pridopidine base.

TABLE 5

Preliminary Composition of Pridopidine IR High Dose Dosage Form

| | | Formulation | |
|---|---|---|---|
| | Use | D (67.5 mg) | E (112.5 mg) |
| | | Composition (mg/capsule) | |
| Pridopidine HCl | API | 76.2 | 127.0 |
| Silicified Micro-crystalline Cellulose (Prosolv ® SMCC 90) | Filler | 129.8 | 79.0 |
| Magnesium Stearate | Lubricant | 4.0 | 4.0 |
| Total | | 210.0 | 210.0 |
| Capsule Size | | 2 | 2 |

Pridopidine drug substance is highly soluble in water. Therefore, the expectation was that wet granulation should not affect the dissolution rate of pridopidine. The dissolution rates of Formulations D and E in phosphate buffer pH 6.8 are shown in Table 6.

The dissolution rate of Formulation D was acceptable with a release profile of greater than 80% after 30 minutes, however, the release profile of Formulation E was suboptimal with only 35% of pridopidine released after 30 minutes and only 58% of pridopidine released after 120 minutes. The significantly slower dissolution rate (35% after 30 min) after wet granulation was unexpected.

TABLE 6

Dissolution Rate of a high dose IR Preliminary Formulation of Pridopidine phosphate buffer pH 6.8

| | % Dissolution (Drag Release %) | | | | | |
|---|---|---|---|---|---|---|
| Time (min) | 0 | 15 | 30 | 60 | 90 | 120 |
| Formulation D 67.5 mg | 0 | 75 | 91 | 100 | | |
| Formulation E 112.5 mg | 0 | 24 | 35 | 44 | 52 | 58 |

Example 4: Pridopidine Immediate Release High Dose Capsules

In an attempt to improve dissolution of the 112.5 mg dosage form of Example 3, a disintegrant was added to Formulation D and Formulation E, to obtain Formulation F and Formulation G (Table 7, below). The process used in Example 3 is used in this example, except that a disintegrant is added. The solids of Formulations F and G are in the form of a powder and granulation powder which are granules.

TABLE 7

Composition of Pridopidine IR High Dose Dosage Form

| | | Formulation | |
|---|---|---|---|
| Batch No. | Use | F (67.5 mg) | G (112.5 mg) |
| | | Composition (mg/capsule) | |
| Pridopidine HCl | Active ingredient | 76.2<br>36% | 127.0<br>60% |
| Silicified Micro-crystalline Cellulose (Prosolv ® SMCC 90) | Filler | 125.8<br>60% | 75.0<br>36% |
| Croscarmellose (Ac-Di-Sol ®) | Disintegrant | 6.0<br>2.9% | 6.0<br>2.9% |
| Magnesium Stearate | Lubricant | 2.0<br>1.0% | 2.0<br>1.0% |
| Total | | 210.0 | 210.0 |
| Capsule Size | | 2 | 2 |

In Formulations F and G, pridopidine was released in 5 min in phosphate buffer pH 6.8 (Table 8). Thus, the disintegrant solved the dissolution problem identified with Formulation E, discussed in Example 3.

TABLE 8

Dissolution Rate of High Dose IR Formulations of Pridopidine in phosphate buffer pH 6.8

| | % Dissolution | | |
|---|---|---|---|
| Time (min) | 0 | 5 | 10 |
| Formulation F 67.5 mg | 0 | 98 | 102 |
| Formulation G 112.5 mg | 0 | 98 | 101 |

The pridopidine active pharmaceutical ingredient (API, pridopidine hydrochloride) is sticky and thus the use of a binder was not needed. However, when the API was condensed into a small volume, the release of the API was impeded, as demonstrated by the dissolution rate of the 112.5 mg capsules of Formulation E (Table 6). This problem was solved by adding a disintegrant as demonstrated in Formulations F and G.

Summary: Two high dose formulations, 67.5 mg and 112.5 mg of pridopidine immediate release, were developed. Using dry granulation, an amount of 67.5 mg pridopidine could be encapsulated in capsule 1 elongated (0.54 ml volume) while the 45 mg dose was encapsulated in capsule 2 having a volume of 0.37 ml. Such a capsule size could not encapsulate a higher dose (>67.5 mg) of dry granulated pridopidine. It was surprising to discover that an amount of 112.5 mg pridopidine could be encapsulated in capsule no. 2 (0.37 ml), if prepared by wet granulation, however, the stickiness of the API delayed its release. The significantly slower dissolution rate (35% after 30 min) after wet granulation was unexpected from a drug substance having the high solubility that pridopidine has. To resolve this issue, disintegrant was added into the wet granulation formulation. Use of a disintegrant in the high dose formulations enabled immediate release of active material.

Example 5: Composition of IR High Dose Pridopidine Dosage Forms

Additional immediate release dosage forms are prepared having the compositions disclosed in Tables 9-12. The dosage forms in Tables 9-12 comprise the equivalent of 67.5 mg, 75 mg, 90 mg, 100 mg, 112.5 mg, 125 mg, 135 mg, 150 mg, 175 mg, 180 mg or 200 mg of pridopidine base. The capsules are size 1 or smaller, or size 2 and are easy to swallow and easy to handle. The compositions disclosed in Tables 9-12 were prepared by the granulation method disclosed in Example 4.

TABLE 9

Examples of Composition of IR High Dose Pridopidine Dosage Forms

| | Formulation | | | | |
|---|---|---|---|---|---|
| | 67.5 mg capsules | 75 mg capsules | 90 mg capsules | 100 mg capsules | 112.5 mg capsules |
| | Composition | | | | |
| | mg/capsule | mg/capsule | mg/capsule | mg/capsule | mg/capsule |
| Pridopidine HCl | 76.2 | 84.7 | 101.6 | 112.9 | 127 |
| Silicified Micro-crystalline Cellulose (Prosolv ® SMCC 90) | 125.8 | 117.3 | 100.4 | 89.1 | 75 |
| Croscarmellose (Ac-Di-Sol ®) | 6 | 6 | 6 | 6 | 6 |
| Magnesium Stearate | 2 | 2 | 2 | 2 | 2 |
| Total | 210 | 210 | 210 | 210 | 210 |
| Capsule Size | 2 | 2 | 2 | 2 | 2 |

The dosage forms in Table 9 provide solid unit dosage forms having a volume of 0.37 ml and comprise 76.2 mg to 127 mg pridopidine HCl.

TABLE 10

Examples of Compositions of IR High Dose Pridopidine Dosage Forms

| | Formulation | | | | |
|---|---|---|---|---|---|
| | 67.5 mg capsules | 75 mg capsules | 90 mg capsules | 100 mg capsules | 112.5 mg capsules |
| | Composition | | | | |
| | mg/capsule | mg/capsule | mg/capsule | mg/capsule | mg/capsule |
| Pridopidine HCl | 76.2 | 84.7 | 101.6 | 112.9 | 127 |
| Silicified Micro-crystalline Cellulose (Prosolv ® SMCC 90) | 45.8 | 50 | 60 | 67 | 75 |
| Croscarmellose (Ac-Di-Sol ®) | 3.5 | 4 | 5 | 5.6 | 6 |
| Magnesium Stearate | 1 | 1 | 1.4 | 2 | 2 |
| Total | 126.5 | 139.7 | 168 | 187.5 | 210 |
| Capsule Size | 4 | 4 or 4el | 4el or 3 | 3 | 2 |

The dosage forms in Table 10 provide solid unit dosage forms having a volume of 0.21 ml to 0.37 ml and comprise 76.2 mg to 127 mg pridopidine HCl.

TABLE 11

Examples of Compositions of IR High Dose Pridopidine Dosage Forms

| | Formulation | | | | |
|---|---|---|---|---|---|
| | 100 mg capsules | 125 mg capsules | 135 mg capsules | 150 mg capsides | 175 mg capsules |
| | Composition | | | | |
| | mg/capsule | mg/capsule | mg/capsule | mg/capsule | mg/capsule |
| Pridopidine HCl | 112.8 | 141.1 | 152.4 | 169.3 | 197.4 |
| Silicified Microcrystalline Cellulose (Prosolv ® SMCC 90) | 89.2 | 60.9 | 49.6 | 50.7 | 110 |
| Croscarmellose (Ac-Di-Sol ®) | 6 | 6 | 6 | 6 | 8 |
| Magnesium Stearate | 2 | 2 | 2 | 2 | 3.5 |
| Total | 210 | 210 | 210 | 228 | 318.9 |
| Capsule Size | 2 | 2 | 2 | 2 or 2el | 2 el or 1 |

The dosage forms in Table 11 provide solid unit dosage forms having a volume of 0.37 ml to 0.54 ml and comprise 112.8 mg to 197.4 mg pridopidine HCl.

TABLE 12

Examples of Compositions of IR High Dose Pridopidine Dosage Forms

| | Formulation | | | | | |
|---|---|---|---|---|---|---|
| Composition | 125 mg capsules mg/capsule | 135 mg capsules mg/capsule | 150 mg capsules mg/capsule | 175 mg capsules mg/capsule | 180 mg capsules mg/capsule | 200 mg capsules mg/capsule |
| Pridopidine HCl | 141.1 | 152.4 | 169.3 | 197.4 | 203.2 | 225.6 |
| Silicified Microcrystalline Cellulose (Prosolv ® SMCC 90) | 83.3 | 90 | 100 | 110 | 120 | 133.3 |
| Croscarmellose (Ac-Di-Sol ®) | 6 | 7 | 7 | 8 | 8 | 8 |
| Magnesium Stearate | 2 | 2.5 | 2.5 | 3 | 3.5 | 3.5 |
| Total | 232.4 | 251.2 | 278.8 | 318.4 | 334.7 | 370.4 |
| Capsule Size | 2.2el or 1 | 2el or 1 | 1 | 1 or 1el | 1el | 1el |

The dosage forms in Table 12 provide solid unit dosage forms having a volume of 0.37 ml to 0.54 ml and comprise 141.1 mg to 225.6 mg pridopidine HCl.

Example 6: IR High Dose Pridopidine Dosage Forms Comprising Mini-Tablets

Immediate release (IR) mini-tablet formulation, containing pridopidine base or pridopidine salt (HCl), encapsulated in a capsule shell (i.e. gelatin), or packaged for example in a sachet. The IR mini tablets are designed for pediatric and the elderly populations. The mini-tablets may be uncoated or coated. The IR mini-tablets provide a dissolution profile of NLT 80% release within 30 minutes. The IR mini-tablets preferably provide a dissolution profile of NLT 85% release within 15 minutes.

The example provided herein provides for coated IR mini-tablets, filled into a gelatin capsule shell, a sachet or other package type for oral administration. Exemplary coatings include polyvinyl acetate based coatings, polyvinyl alcohol based coatings, ethyl cellulose based coatings, copolymers derived from esters of acrylic and methacrylic acid based coatings and include brands Kollicoat® Smartseal 30 D, Eudragit® EPO, Opadry® and Ethocel®.

Mini-tablets were formed by granulating a blend containing pridopidine hydrochloride, silicified microcrystalline cellulose, croscarmellose sodium as disintegrant and magnesium stearate followed by compressing, see composition in Table 13.

TABLE 13

Composition of IR mini-tablets

| | Composition | | |
|---|---|---|---|
| | Core | | |
| Materials | mg/tablet | mg/capsule | (%) |
| Pridopidine HCl | 0.971 | 127.0[a] | 60.5 |
| Silicified Microcrystalline Cellulose(Prosolv ® SMCC90) | 0.574 | 75.0 | 35.7 |
| Croscarmellose Sodium (Ac-Di-Sol ®) | 0.046 | 6.0 | 2.9 |

TABLE 13-continued

Composition of IR mini-tablets

| | Composition | | |
|---|---|---|---|
| | Core | | |
| Materials | mg/tablet | mg/capsule | (%) |
| Magnesium stearate | 0.015 | 2.0 | 1.0 |
| Theoretical weight | 1.606 | 210.0 | 100% |
| Punch | 1.2 mm | — | — |

[a]Equivalent to 112.5 mg Pridopidine base

The disintegrant may be added either prior to granulation (intragranular 2-4%) or prior to compression (after granulation i.e. extragranular 1-3%) or at both processing steps (up to about 7% by weight of total dosage form).

The coating step was carried out using the composition shown in Table 14.

TABLE 14

Composition of coating solution on mini-tablet

| Raw Materials | Coating solution (g) 400 g total | 0.5% coating (R2) Coating material mg/tablet | 1.0% coating (R3) mg/tablet |
|---|---|---|---|
| Ethocel Premium 7 CPS PH.EUR | 318.0 | 0.00636 | 0.01277 |
| Polyethylene Glycol 400 NF | 64.7 | 0.00129 | 0.00259 |
| Triacetin USP | 17.0 | 0.00034 | 0.00068 |
| Solid remained on tablet | | 0.008 | 0.01606 |

The dissolution results and profiles of the mini-tablet compositions are shown in Table 15. R1 is an immediate release batch of core mini tablets, uncoated. R2 was obtained from R1 with 0.5% coating and R3 from R1 with 1.0% coating.

TABLE 15

Dissolution Rate of IR Mini Tablets in Phosphate buffer pH6.8

| Batch Name | Time (min) | | | |
|---|---|---|---|---|
| | 0 | 4 | 10 | 30 |
| R1 (Core mini tablet) | 0 | 97 | 98 | 100 |
| R2 (0.5% coating) | 0 | 88 | 97 | 98 |
| R3 (1.0% coating) | 0 | 67 | 91 | 99 |

Each mini-tablet weighs about 1.6 mg and includes about 1 mg pridopidine or equivalent amount pridopidine salt. The mini-tablets are packaged by desired dose in a suitable package, i.e. capsule (gelatin or other), sachet.

Example 7: 75 mg, 100 mg, 150 mg Pridopidine Dosage Forms in Size 2 Capsule

Size 2 capsules including high dose (75 mg, 100 mg and 150 mg) of pridopidine or pridopidine salt (HCl) were prepared using a wet granulation process. Dry mix process did not address the need to produce high dose of drug substance in small size capsule to meet patient needs.

The process for the preparation of the size 2 capsules including high dose (75 mg, 100 mg and 150 mg) of pridopidine or pridopidine salt (HCl) include the following steps:

Dry Premix: Pridopidine HCl, silicified microcrystalline cellulose (Prosolv SMCC90), and Ac-Di-Sol (croscarmellose sodium) were placed into a high-shear mixer and mixed for 5 minutes at mixer speed 200 rpm.

Wet granulation: Purified water was added to the contents of the high-shear granulating mixer together with the dry mix to obtain a wet granulate.

Drying Process: The granulate was dried in a fluid bed dryer to LOD of NMT 1% w/w.

Milling: The granulate was milled using laboratory scale Quadro Comil at a speed of 1500 rpm and 2500 rpm Sieve analysis of granulate samples was measured. The particle size distribution of the samples is presented in FIG. 4. A very slight variation in particle size distribution was observed indicating the process is quite robust.

Final blending and sampling: The milled granulate was finally blended with extra-granular excipients and lubricated with magnesium stearate at 15 rpm for 5 min.

Encapsulation: The different batches of 67.5 mg, 90 mg, 75 mg dose, 100 mg dose, 150 mg dose, were encapsulated at 200±10 mg of granulate into size 2 capsules. The encapsulation of prototype batches was conducted using automated encapsulator. No plug formation was observed during granulate encapsulation

TABLE 16

Formulation comprising 75 mg, 100 mg and 150 mg Pridopidine in a Capsule Size 2.

| Component | Function | 75 mg (pridopidine free) mg/capsule | 100 mg (pridopidine free) mg/capsule | 150 mg (pridopidine free) mg/capsule |
|---|---|---|---|---|
| Pridopidine-HCl, mg (%) | Drug Substance | 84.8 mg 42% | 113.0 mg 57% | 169.5 mg 85% |
| Silicified microcrystalline cellulose, mg (%) | Filler | 105.25 mg 53% | 77.00 mg 39% | 20.50 mg 10% |
| Ac-Di-Sol, mg (%) | Disintegrant | 8.0 mg 4% | 8.0 mg 4% | 8.00 mg 4% |
| Magnesium stearate, (mg) % | | 2.0 mg 1% | 2.0 mg 1% | 2.0 mg 1% |
| Total fill weight | | 200.00 mg | 200.00 mg | 200.00 mg |
| Hard gelatine capsule, white, | | 1 unit size 2 | 1 unit size 2 | 1 unit size 2 |
| Gelatine | | Approx. 61 mg | Approx. 61 mg | Approx. 61 mg |
| Titanium dioxide | | Approx. 2.0% | Approx. 2.0 | Approx. 2.0 |

*The supplied API is a hydrochloride salt form. For converting the amount of pridopidine HCl (mg) into the amount of pridopidine as free base (mg), the following correction factor was used 0.885

Figure 1:
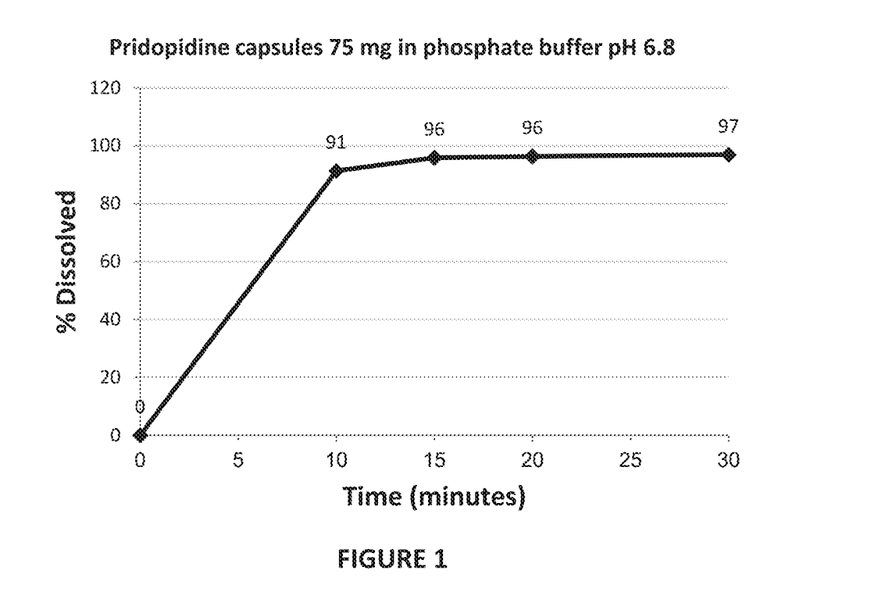
FIG. 1 is a dissolution profile of % dissolved for 75 mg size 2 capsules in phosphate buffer pH 6.8).
Figure 2:
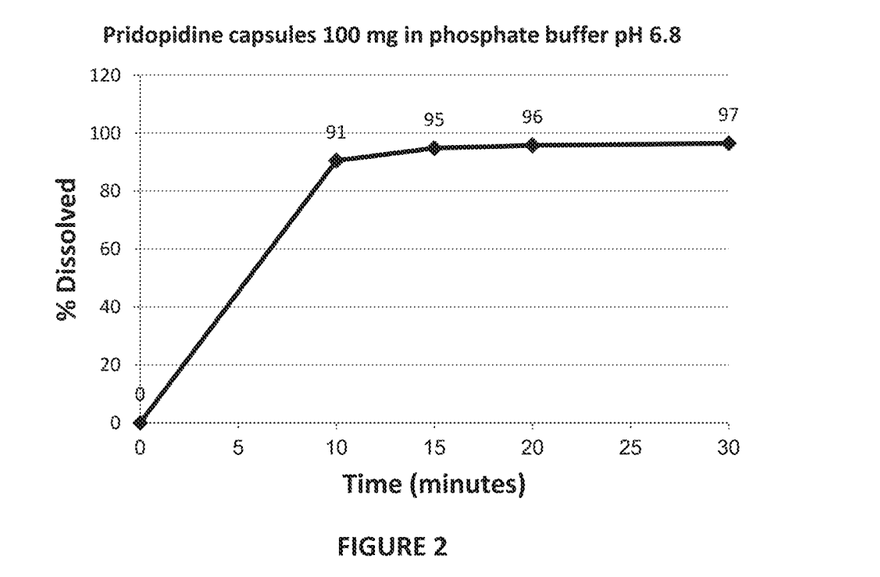
FIG. 2 is a dissolution profile of % dissolved for 100 mg size 2 capsules (in phosphate buffer pH 6.8).
Figure 3:
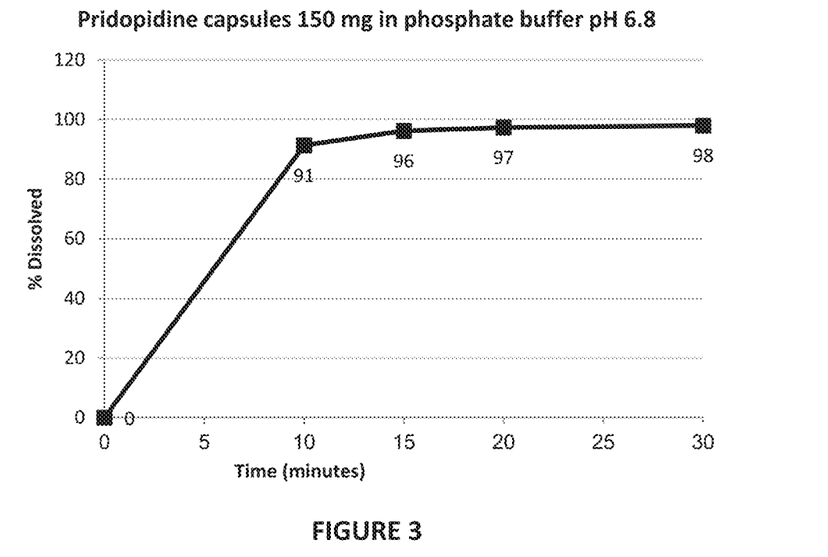
FIG. 3 is a dissolution profile of % dissolved for 150 mg size 2 capsules in phosphate buffer pH 6.8).

Dissolution Testing:

The capsules describe above for 75 mg, 100 mg, 150 mg pridopidine in size 2 capsules were tested for dissolution in phosphate buffer pH 6.8 FIGS. 1-3 present the dissolution plot of the capsules of, giving immediate release profile of the drug product (>85% drug release in 15 min).

REFERENCES

Clinicaltrials.gov Clinical Trial Identifier NCT02006472, "A Phase 2, to Evaluating the Safety and Efficacy of Pridopidine Versus Placebo for Symptomatic Treatment in Patients With Huntington's Disease."

de Yebenes J G, Landwehrmeyer B, Squitieri F, Reilmann R, Rosser A, Barker R A, Saft C, Magnet M K, Sword A, Rembratt A, Tedroff J; MermaiHD study investigators, "Pridopidine for the treatment of motor function in patients with Huntington's disease (MermaiHD): a phase 3, randomised, double-blind, placebo-controlled trial," Lancet Neurol. 2011 December; 10(12):1049-57. doi: 10.1016/S1474-4422(11)70233-2. Epub 2011 Nov. 7.

Geva et al. (2016). Pridopidine activates neuroprotective pathways impaired in Huntington Disease. HIMG 25(18): 3975-87.

Huntington Study Group HART Investigators, "A randomized, double-blind, placebo-controlled trial of pridopidine in Huntington's disease," Mov Disord. 2013 September; 28(10):1407-15. doi: 10.1002/mds.25362. Epub 2013 Feb. 28.

Lindskov Krog P, Osterberg O, Gundorf Drewes P, Rembratt A, Schultz A, Timmer W. "Pharmacokinetic and tolerability profile of pridopidine in healthy-volunteer poor and extensive CYP2D6 metabolizers, following single and multiple dosing" Eur J Drug Metab Pharmacokinet. 2013 March; 38(1):43-51. Epub 2012 Sep. 5.

Mangal et al. "Superdisintegrants: An Updated Review" International Journal of Pharmacy and Pharmaceutical Science Research 2012; 2(2) 26-35.

Mohanachandran et al., "Superdisintegrants: An Overview" International Journal of Pharmaceutical Sciences Review and Research Volume 6, Issue 1, January-February 2011; Article-022.

Osterberg, et al. "A single center, randomized, placebo-controlled, double-blind study to evaluate the safety, tolerability, and pharmacokinetics of multiple-ascending doses of pridopidine in healthy volunteers" Poster presented at Sixth Annual Huntington Disease Clinical Research Symposium, November 2012, Seattle, Wash., USA. Neurotherapeutics.

U.S. Pat. No. 6,903,120, issued Jun. 7, 2005, Sonesson, et al.

U.S. Pat. No. 7,923,459, issued Apr. 12, 2011, Gauthier, et al.

U.S. Patent Application Publication No. US-2013-0267552-A1, published Oct. 10, 2013, Waters et al.

US Patent Application Publication No. US-2014-0378508-A1, published Dec. 25, 2014, Bassan et al.

US Patent Application Publication No. 2015-0202302-A1, published Jul. 23, 2015, Licht et al.

USP <711> DISSOLUTION. 2016. 33(4) Fourth Interim Revision Announcement. Nov. 21, 2016.

CSID:25948790, http://www.chemspider.com/Chemical-Structure.25948790.html (accessed 23:27, Jul. 15, 2016).

CSID:7971505, http://www.chemspider.com/Chemical-Structure.7971505.html (accessed 23:33, Jul. 15, 2016).

The invention claimed is:

1. A solid unit high dose immediate release dosage form comprising pridopidine and at least one pharmaceutically acceptable excipient and a disintegrant; wherein the disintegrant is a superdisintegrant selected from the group consisting of: croscarmellose sodium, crospovidone, and polacrilin potassium; wherein the disintegrant is present in an amount of about 1% to 10% by weight of the solid unit dosage form; wherein the dosage form has a volume and wherein the amount of pridopidine of the dosage form is 135-600 mg per ml of volume of the dosage form and wherein 80-100% of the pridopidine is released within 30 minutes as measured using a USP#2 dissolution apparatus.

2. The solid unit dosage form of claim 1, wherein the solid unit dosage form comprises between 135-400 mg of pridopidine per ml of volume of the dosage form.

3. The solid unit dosage form of claim 1, wherein the solid unit dosage form comprises between 175-370 mg of pridopidine per ml of volume of the dosage form.

4. The solid unit dosage form of claim 1, wherein the solid unit dosage form comprises about 67.5 mg, about 75 mg, about 90 mg, about 100 mg, about 112.5 mg, about 125 mg, about 135 mg, about 150 mg, 175 mg, about 180 mg or about 200 mg of pridopidine.

5. The solid unit dosage form of claim 1 wherein: a) the volume of the dosage form is 0.5 ml and the solid unit dosage form comprises 90-200 mg pridopidine; b) the volume of the dosage form is 0.37 ml and the solid unit dosage form comprises 67.5-200 mg pridopidine; c) the volume of the dosage form is 0.30 ml and the solid unit dosage form comprises 67.5-180 mg pridopidine; d) the volume of the dosage form is 0.21 ml and the solid unit dosage form comprises 67.5-135 mg pridopidine; or e) the volume of the dosage form is 0.13 ml and the solid unit dosage form comprises 67.5 mg pridopidine.

6. The solid unit dosage form of claim 1, wherein the solid unit dosage form is in the form of a tablet or a gelatine capsule.

7. The solid unit dosage form of claim 6, wherein the solid unit dosage form is in the form of a tablet, or a tablet coated with an overcoat layer.

8. The solid unit dosage form of claim 1, wherein the pharmaceutically acceptable excipient is selected from the group consisting of: filler, glidant, lubricant, disintegrant and mixtures thereof.

9. The solid unit dosage form of claim 8, wherein the filler is selected from the group consisting of: microcrystalline cellulose, sugar spheres, lactose, sorbitol, dextrose, sucrose, mannitol, dibasic or tribasic calcium phosphate, calcium sulfate, starch, retalac and mixtures thereof.

10. The solid unit dosage form of claim 9, wherein the filler is silicified microcrystalline cellulose.

11. The solid unit dosage form of claim 8, wherein the filler is present in an amount of about 10% to 80% by weight of the solid unit dosage form, or about 15% to 80% by weight of the solid unit dosage form, or between 26% and 46% by weight of the solid unit dosage form, or is about 36% by weight of the solid unit dosage form, or is between 50% and 70% by weight of the solid unit dosage form, or is about 60% by weight of the solid unit dosage form.

12. The solid unit dosage form of claim 8, wherein the lubricant is selected from the group consisting of: sodium stearyl fumarate, stearic acid, magnesium stearate, calcium stearate, zinc stearate, talc, glyceryl behenate, glyceryl monostearate, and mixtures thereof.

13. The solid unit dosage form of claim 12, wherein the lubricant is magnesium stearate.

14. The solid unit dosage form of claim 13, wherein the lubricant is present in an amount of about 0.5% to 2.0% by weight of the solid unit dosage form, or wherein the lubricant is present in an amount of about 0.5% to 1.5% by weight of the solid unit dosage form, or wherein the lubricant is present in an amount of about 1.0% by weight of the solid unit dosage form.

15. The solid unit dosage form of claim 1, wherein the disintegrant is present in an amount of about 1.9% to 3.6% by weight of the solid unit dosage form.

16. The solid unit dosage form according to claim 1, wherein the pridopidine is provided as pridopidine base or pridopidine salt.

17. The solid unit dosage form according to claim 1, wherein the pridopidine is pridopidine hydrochloride.

18. The solid unit dosage form according to claim 6, wherein the unit dosage form is a capsule having a volume of 0.37 ml and comprising 76.2 mg to 200 mg pridopidine HCl.

19. The solid unit dosage form of claim 18, having a volume of 0.37 ml and comprising 85 mg, 113 mg or 170 mg pridopidine HCl.

20. The solid unit dosage form of claim 1 comprising granules produced by a wet granulation process.

21. The solid unit dosage form of claim 1, wherein the solid unit dosage form is adapted for twice or thrice daily administration.

22. A method of attenuating a symptom or reducing disease progression in a subject afflicted with a condition selected from Huntington's Disease, Parkinson's disease, iatrogenic and non-iatrogenic Parkinsonism, dyskinesias, drug induced-dyskinesias, dystonias, Tourette's disease, iatrogenic and non-iatrogenic psychoses and hallucinoses, schizophrenia disorder or schizophreniform disorder, mood and anxiety disorders, manic depressive illness, depression, obsessive-compulsive disease, a sleep disorder, autism spectrum disorder, ADHD, age-related cognitive impairment, abuse of alcohol and substances used as narcotics, Alzheimer's disease and Retts syndrome, wherein the method comprises administering the solid unit dosage form of claim 1 to the subject.

23. A method of attenuating a symptom or reducing disease progression in a subject afflicted with a neurodegenerative disease or a disease related to dopamine, comprising once daily administration of the solid unit dosage form of claim 1.

24. A process for preparing the granules of claim 20, the process comprising forming a wet granulate.

25. The process of claim 24, further comprising mixing pridopidine with a solution of water and/or an organic solution, with or without a binder, and optionally an intragranular excipient to form a wet granulate.

26. The process of claim 24, wherein the process comprises an intragranular excipient and wherein the intragranular excipient is a filler, a disintegrant or a combination thereof.

* * * * *